(12) United States Patent
Huening et al.

(10) Patent No.: US 9,585,559 B2
(45) Date of Patent: *Mar. 7, 2017

(54) IMAGING ACCESSORY FRAME FOR INTEGRATION WITH AN OPERATING MICROSCOPE

(71) Applicant: Bioptigen, Inc., Morrisville, NC (US)

(72) Inventors: Pete Huening, Clayton, NC (US); Eric L. Buckland, Hickory, NC (US); Robert H. Hart, Cary, NC (US)

(73) Assignee: Bioptigen, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/805,633

(22) Filed: Jul. 22, 2015

(65) Prior Publication Data

US 2015/0320312 A1 Nov. 12, 2015

Related U.S. Application Data

(63) Continuation of application No. 13/334,678, filed on Dec. 22, 2011, now Pat. No. 9,107,618.

(60) Provisional application No. 61/426,192, filed on Dec. 22, 2010.

(51) Int. Cl.
*A61B 3/14* (2006.01)
*A61B 3/12* (2006.01)
*A61B 3/10* (2006.01)
*A61B 3/13* (2006.01)

(52) U.S. Cl.
CPC ............ *A61B 3/1225* (2013.01); *A61B 3/102* (2013.01); *A61B 3/13* (2013.01)

(58) Field of Classification Search
CPC ......... A61B 3/152; A61B 3/145; A61B 3/103; A61B 3/1015; A61B 3/14; A61B 3/12
USPC .................. 351/200, 205, 206, 208, 246
See application file for complete search history.

(56) References Cited

U.S. PATENT DOCUMENTS

| | | | | |
|---|---|---|---|---|
| 3,762,798 A * | 10/1973 | Grubb et al. | | 359/394 |
| 4,972,258 A * | 11/1990 | Wolf et al. | | 348/79 |
| 7,447,408 B2 * | 11/2008 | Bouma et al. | | 385/123 |
| 8,064,989 B2 | 11/2011 | Brown et al. | | |
| 2005/0231727 A1 * | 10/2005 | Podoleanu et al. | | 356/479 |
| 2006/0132790 A1 * | 6/2006 | Gutin | | 356/479 |
| 2007/0081166 A1 | 4/2007 | Brown et al. | | |
| 2009/0141237 A1 | 6/2009 | Izatt et al. | | |
| 2009/0268020 A1 | 10/2009 | Buckland et al. | | |

\* cited by examiner

*Primary Examiner* — James Greece
(74) *Attorney, Agent, or Firm* — Ward and Smith, P.A.

(57) ABSTRACT

An accessory frame for selectively coupling components to an optical microscope for imaging of a subject is provided. The optical microscope has a body including an undercarriage. The accessory frame includes a mounting plate that attaches to the undercarriage of the microscope. The mounting plate includes a first attachment port and a second attachment port. The first attachment port is configured to couple a first optical assembly in an optical path of the microscope between an objective lens of the microscope and the subject. The second attachment port is configured to couple a second optical assembly to the microscope body with at least a portion of the optical path of the second optical assembly being outside of the optical path of the microscope.

5 Claims, 17 Drawing Sheets

122 (top)

122 (bottom)

132

IMAGING ACCESSORY FRAME FOR INTEGRATION WITH AN OPERATING MICROSCOPE

CLAIM OF PRIORITY

The present application is a continuation of U.S. application Ser. No. 13/334,678, filed Dec. 22, 2011, which claims priority from U.S. Provisional Application No. 61/426,192, filed Dec. 22, 2010, the disclosures of which are hereby incorporated herein by reference as if set forth in their entireties.

FIELD

The present inventive concept relates to imaging and, more particularly, to frames for use in the imaging process.

BACKGROUND

Surgical microscopes provide a magnified view of the operating field to the surgeon. Ophthalmic surgical microscopes are commonly stereo zoom microscopes with binocular view ports for the surgeon, and frequently have one or two observer view ports at ninety degrees (left and right) to the surgeon. The working distance between the objective lens of the microscope and the surface of a patient eye may range from about 100 mm to about 200 mm. At this working distance, which provides a suitable field of access for the manual work of the surgeon, the field of view within a patient eye may be quite limited. It is quite common to then use an intermediate lens, such as the Binocular Indirect Ophthalmo Microscope (BIOM) of Oculus Optikgerat, to modify the magnification and field of view for the surgeon. This intermediate lens is mounted to the under-carriage of the microscope head, and includes mechanics to adjust focus, and to flip the lens into and out of the field of view of the microscope.

Other illumination or imaging devices may also be used in the surgical field. Ideally, all illumination and imaging sources would be directly integrated coaxial to and within the optical path of the operating microscope, without impacting the operating field for the surgeon, the observers, the anesthesiologists, and the like. This is not always possible. Without full integration as such, it is still desirable to provide a readily maneuverable mount for imaging and other accessories that is closely coupled to the surgical field, and the mechanical controls and attributes that are already integral to a well-functioning operating microscope.

A particular case of interest is the incorporation of optical coherence tomography (OCT) imaging into the surgical visualization practice. OCT provides high resolution imaging of ocular tissue microstructure, and is showing great promise to provide information to the surgeon that will improve therapeutic outcomes, and reduce the total economic burdens of surgery by reducing risk and reducing re-work. The current generation of OCT, known generally as Fourier Domain OCT, provides very fast volumetric images (>30 mega-voxels per second) at very high resolution (2.0 µm to 6.0 µm axial resolution, 10.0 µm to 20 µm lateral resolution) particularly well suited to visualizing the fine tissue layers and membranes that are often the subject of the surgical effort. In contrast to microscope visualization, OCT provides depth-resolved images, highlighting subsurface physiology and pathology, with full volumes over a 30 to 70 degree field of view acquired in about 1 to 3 seconds. However, the alignment requirements of OCT, particularly for retina imaging, but also for cornea imaging, may be quite demanding to obtain high quality images. A flexible, finely controlled, and stable imaging platform is desirable.

At present, there are no commercially available operating microscopes with integrated OCT capabilities. The Assignee of the present application has demonstrated handheld OCT imaging as discussed in, for example, U.S. Patent Application Publication No. 2007/0081166 entitled PORTABLE OPTICAL COHERENCE TOMOGRAPHY (OCT) DEVICES AND RELATED SYSTEMS; U.S. Patent Application Publication No. 2009/0268020 entitled OPTICAL COHERENCE TOMOGRAPHY (OCT) IMAGING SYSTEMS FOR USE IN PEDIATRIC OPHTHALMIC APPLICATIONS AND RELATED METHODS AND COMPUTER PROGRAM PRODUCTS; and U.S. Patent Application Publication No. 2009/0141237 entitled INTEGRATED OPTICAL COHERENCE IMAGING SYSTEMS FOR USE IN OPHTHALMIC APPLICATIONS AND RELATED METHODS AND COMPUTER PROGRAM PRODUCTS. Devices discussed therein are finding increasing utility in the operative field. However, in some embodiments, the handheld device may be relatively difficult to align and stabilize for imaging in the operating field.

Approaches have been established to address the stabilization issue. For example, one approach to stabilize a handheld probe is to use a simple planar mount coupled to the objective lens of the microscope. This device has a fixed armature length, and coarsely rotates around the lens. There are no height adjustments, and there is no ballast to control torque on the microscope head. Another approach has been adopted by Optovue. This approach uses an articulating arm attached to a structure other than the operating microscope. This approach lacks the fine control afforded by a well engineered operating microscope, and risks being obstructive to the broader operating field. A third approach has been to use an independent boom mount, with balance similar to an operating microscope, as illustrated in, for example, U.S. Pat. No. 8,064,989. This approach may add unnecessary bulk to the limited space of the operating theater.

SUMMARY

Some embodiments of the present inventive concept provide an accessory frame including an optical coherence tomography (OCT) imaging head. The accessory frame includes a mounting plate including a microscope field lens attachment port and a microscope field plate anchor pin. The mounting plate is configured to receive an intermediate field lens in the microscope field lens attachment port such that the accessory frame shares the mounting plate in common with an intermediate field lens.

In further embodiments, the accessory frame may be configured to be mountable such that rotation is to a left or a right of a surgeon.

In still further embodiments, the accessory frame may be configured to rotate about 180 degrees on a half plane perpendicular to an optical axis to a left or a right of a surgeon.

In some embodiments, the accessory frame may be configured to rotate, such that when not in use, the mounted imaging head is about 180 degrees away from a surgeon and about ninety degrees away from any observer stationed along a corresponding half plane.

In further embodiments, the accessory frame may be configured to rotate, such that when in use, a distance between a microscope optical axis and an independent imaging head optical axis is selected by a user.

In still further embodiments, the accessory frame may have a height adjustment configured to position a distal surface of an imaging head objective lens equal to or above a distal surface of a microscope objective lens.

In some embodiments, the accessory frame may have a height adjustment configured to position a distal surface of an imaging head objective lens at an appropriate working distance with respect to a patient eye for proper imaging.

In further embodiments, the accessory frame may have a height adjustment configured to accurately set a working distance from about 0.1 mm to about 1.0 mm.

In still further embodiments, the accessory frame may include at least some sterilized or sterilizable materials suitable for use within a surgical sterile field.

In some embodiments, the accessory frame may include at least some autoclavable or disposable materials suitable for use within a surgical sterile field.

In further embodiments, the accessory frame may further include debris traps configured to catch any materials that abrade from a structure during motion, rotations and/or lifts while within a sterile field.

In still further embodiments, the accessory frame may be configured to be maneuverable with or without the intermediate field lens in place, without requiring any interaction with the intermediate field lens.

In some embodiments, the accessory frame may further include at least one point of rapid connect/disconnect to allow simple, single-handed removal of either the entire frame or the mounted imaging head, without requiring any interaction with the intermediate field lens.

In further embodiments, the accessory frame may further include a ballast configured to balance a weight of the accessory frame including the imaging head, the ballast being applied to the half-plane opposite of the mounting of the frame and imaging head.

BRIEF DESCRIPTION OF THE DRAWINGS

The accompanying drawings, which are included to provide a further understanding of the inventive concept and are incorporated in and constitute a part of this application, illustrate certain embodiment(s) of the inventive concept. In the drawings.

DETAILED DESCRIPTION

Figure 1:
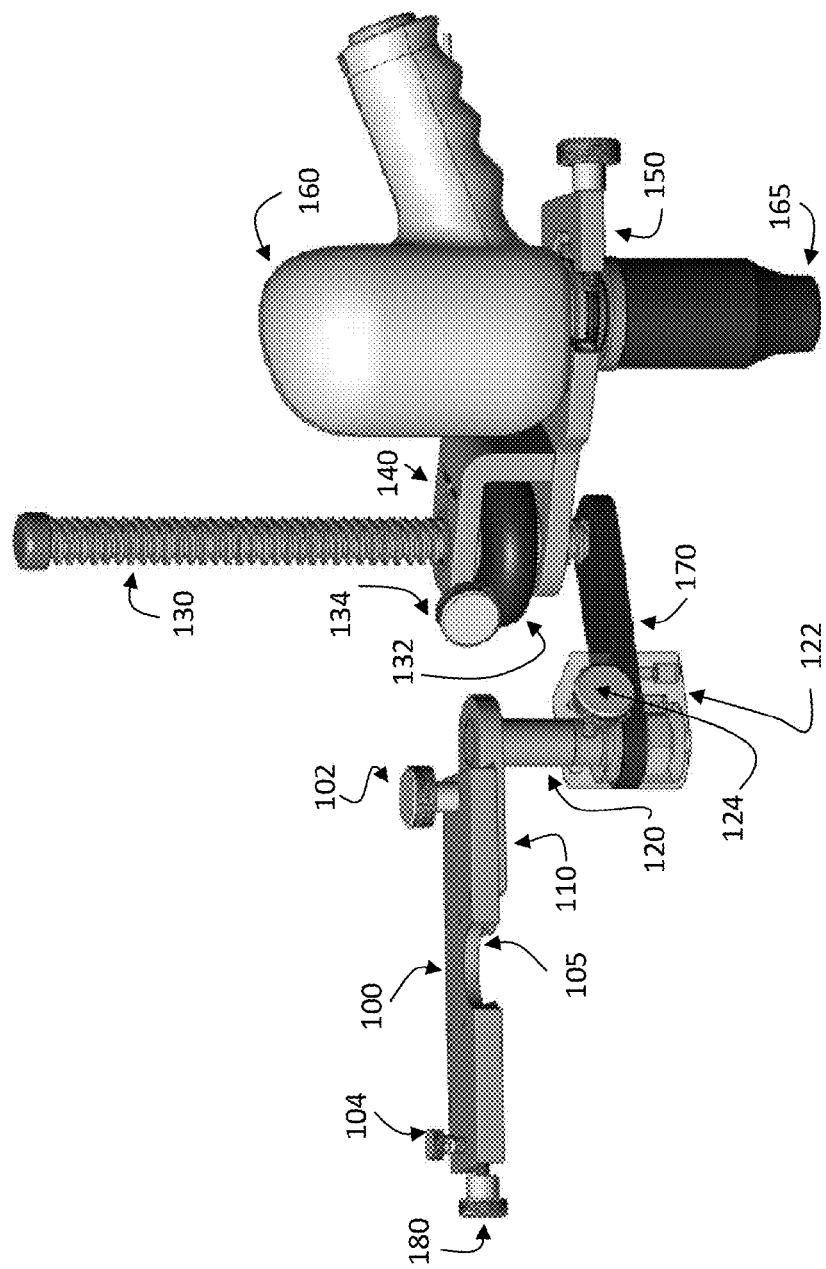
FIG. 1 is a diagram illustrating a surgical mount (accessory frame) including an optical coherence tomography (OCT) imaging head according to some embodiments of the present inventive concept.

The inventive concept will now be described more fully hereinafter with reference to the accompanying drawings, in which embodiments of the inventive concept are shown. This inventive concept may, however, be embodied in many different forms and should not be construed as limited to the embodiments set forth herein; rather, these embodiments are provided so that this disclosure will be thorough and complete, and will fully convey the scope of the inventive concept to those skilled in the art.

It will be understood that, when an element is referred to as being "connected" to another element, it can be directly connected to the other element or intervening elements may be present. In contrast, when an element is referred to as being "directly connected" to another element, there are no intervening elements present. Like numbers refer to like elements throughout.

Spatially relative terms, such as "above", "below", "upper", "lower" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly. Well-known functions or constructions may not be described in detail for brevity and/or clarity.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present inventive concept. As used herein, the term "and/or" includes any and all combinations of one or more of the associated listed items.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

Embodiments of the inventive concept are described herein with reference to schematic illustrations of idealized embodiments of the inventive concept. As such, variations from the shapes and relative sizes of the illustrations as a result, for example, of manufacturing techniques and/or tolerances, are to be expected. Thus, embodiments of the inventive concept should not be construed as limited to the particular shapes and relative sizes of regions illustrated herein but are to include deviations in shapes and/or relative sizes that result, for example, from different operational constraints and/or from manufacturing constraints. Thus, the elements illustrated in the figures are schematic in nature and their shapes are not intended to illustrate the actual shape of a region of a device and are not intended to limit the scope of the inventive concept.

As discussed above, alignment requirements of optical coherence tomography (OCT), particularly for retina imaging, but also for corneal imaging, may be quite demanding to obtain high quality images. Thus, a flexible, finely controlled, and stable imaging platform is desirable. Accordingly, some embodiments of the present inventive concept provide a mounting frame, alignment, and stabilization system that allows an independent imaging system, such as an OCT imaging head, which will be discussed further below with respect to FIGS. 1 through 14.

Figure 2:
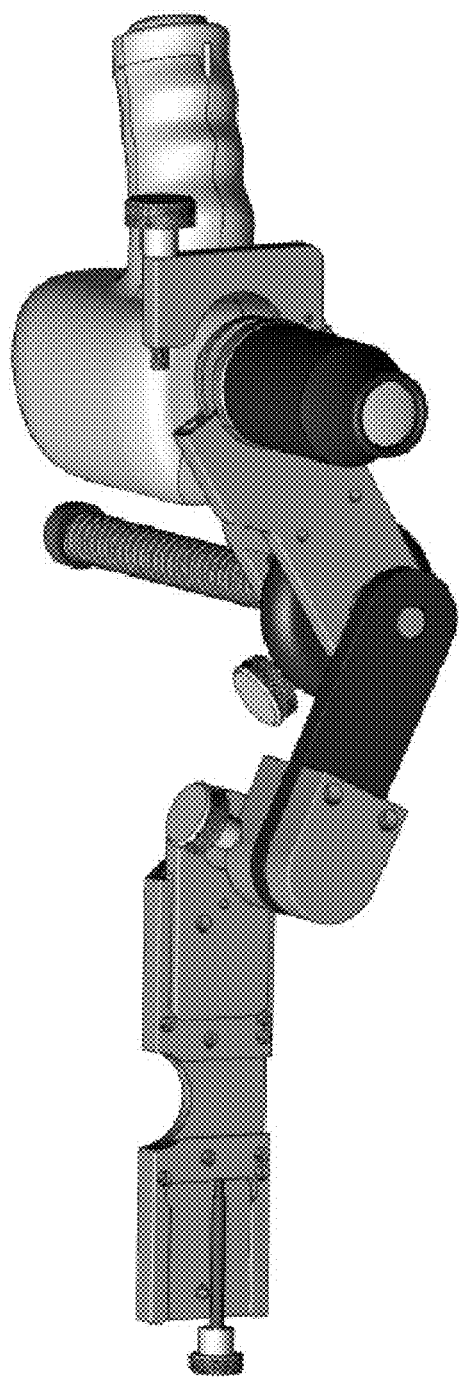
FIG. 2 is a bottom view of the accessory frame of FIG. 1.
Figure 3:
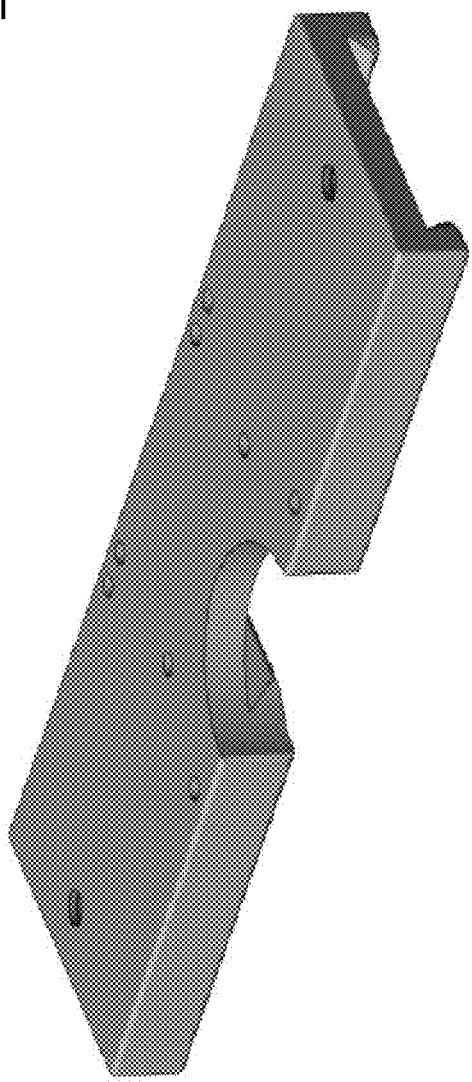
FIG. 3 is a perspective view of a mounting plate of the accessory frame in accordance with some embodiments of the present inventive concept.

Referring first to FIG. 1, diagram illustrating a surgical mount (accessory frame) including an optical coherence tomography (OCT) according to some embodiments of the present inventive concept will be discussed. As illustrated in FIG. 1, the accessory frame 190 includes a mounting plate 100, an accessory frame quick connect plate 110, a first rotation axle 120, a second rotation axle with riser 130, an instrument carriage 140, an instrument carriage quick connect instrument mount 150, an imaging head 160, a debris trap 122, an elevation wheel 132, a first rotation lock 124, a second rotation lock 134, an accessory frame quick connect lock 102, a rotation axle bridge 170, a microscope field lens attachment port (dovetail) 105, a microscope field lens anchor pin/ballast 180, a ballast lock 104 and imaging head lens 165. FIG. 2 is a bottom view of the accessory frame 190 of FIG. 1. Details of many of the aspects of the accessory frame of FIGS. 1 and 2 will be discussed further below with respect to FIGS. 3 through 10. It will be understood that embodiments of the present inventive concept are not limited to the details illustrated in FIGS. 1 and 2. Features may be added or deleted without departing from the scope of the present inventive concept.

Figure 4:
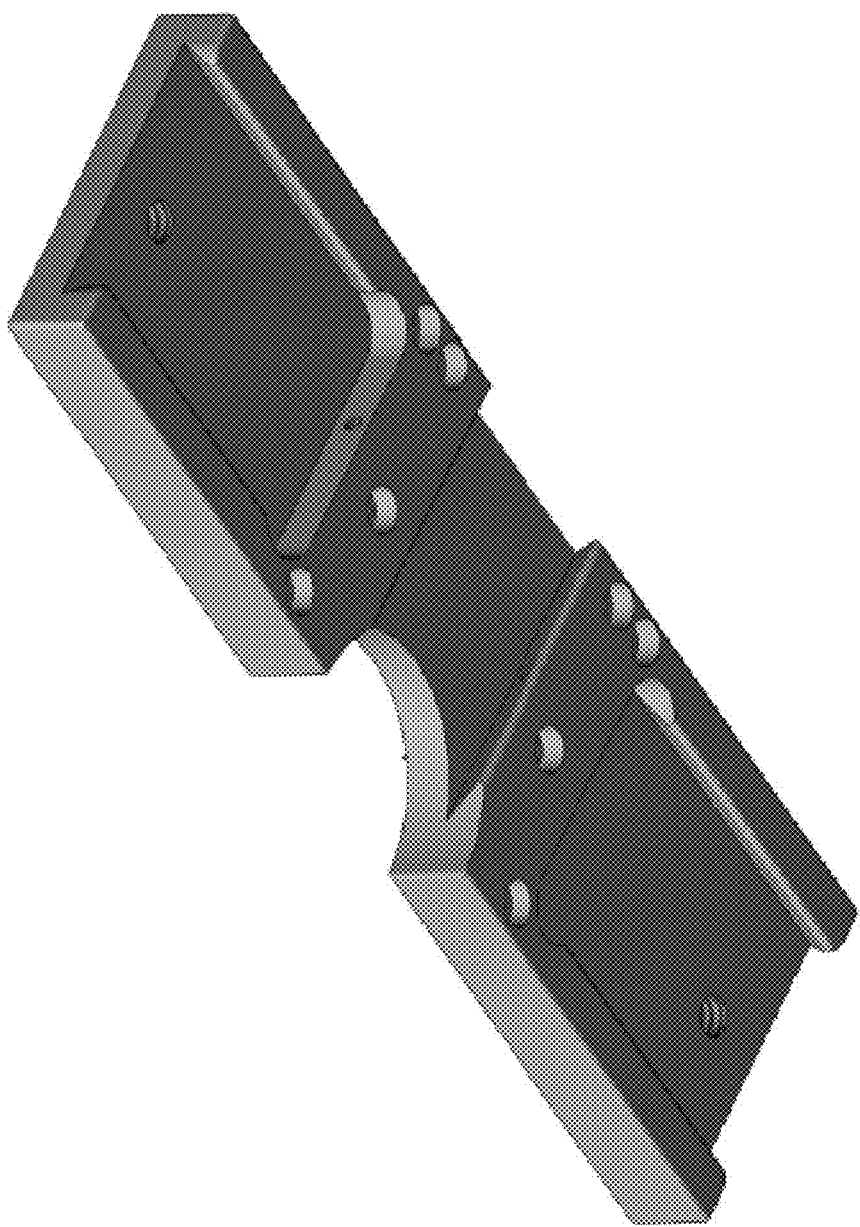
FIG. 4 is a bottom view of a mounting plate of the accessory frame in accordance with some embodiments of the present inventive concept.

As discussed above, improvements in the area of frames and the like are desired. Accessory frames 190 in accordance with some embodiments of the present inventive concept may share a mounting plate in common with an intermediate field lens. In particular, as illustrated in FIGS. 1, the mounting plate 100 includes a microscope field lens attachment port 105. This feature of the mounting plate 100 may be clearer in the enlarged perspective view of the mounting plate 100 illustrated in FIG. 3. FIG. 4 is a diagram illustrating an underside of the mounting plate 100. Thus, an intermediate field lens may be mounted to the accessory frame 190 using the field lens attachment port 105 of the mounting plate 100.

Figure 15:
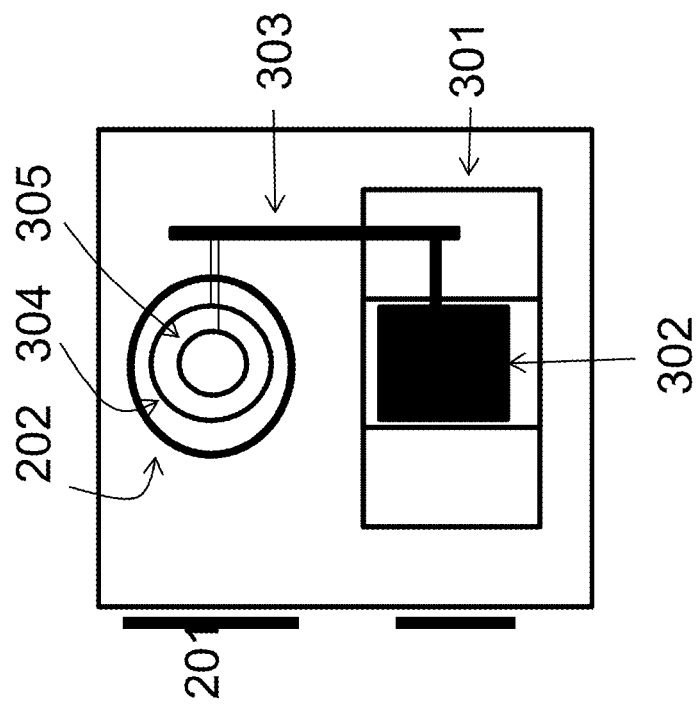
FIG. 15 is block diagram illustrating the placement of the mount to the undercarriage of the microscope imaging body in accordance with some embodiments of the inventive concept.
Figure 15:
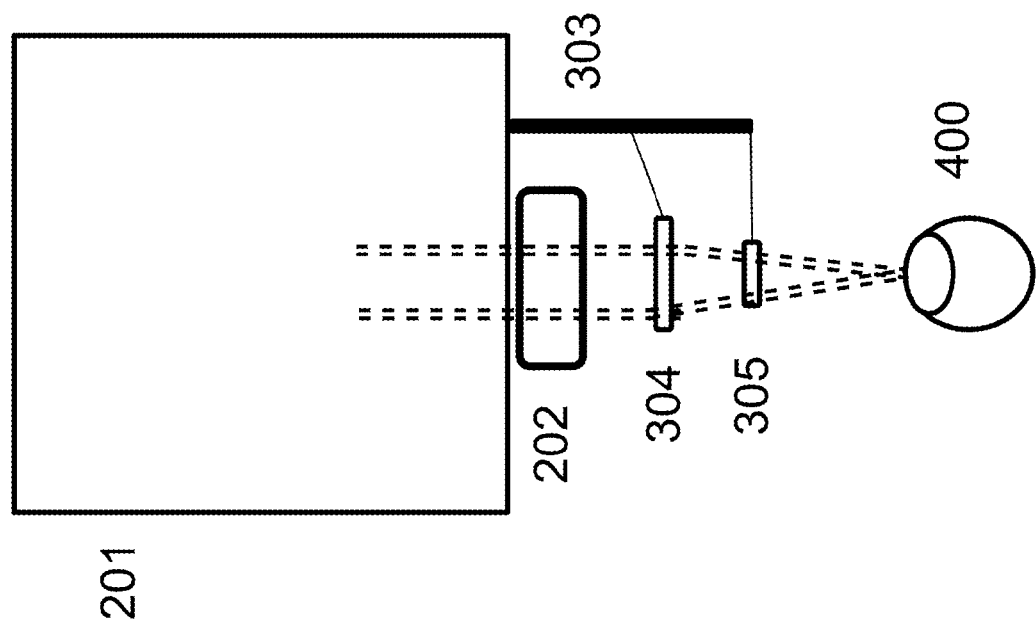

Referring to FIG. 15, a diagram illustrating the placement of the mount 300 (100 in FIG. 1) to the undercarriage of the microscope imaging body 201 will be discussed. As illustrated therein, the field lens assembly 300 includes the dovetail plate 302, and armature 301 that holds a reducing lens 304 and a final objective in the field between the microscope objective 202 and the subject 400. Other optical assemblies may be used mounted to the carriage 302 without departing from the scope of the present inventive concept.

Figure 16:
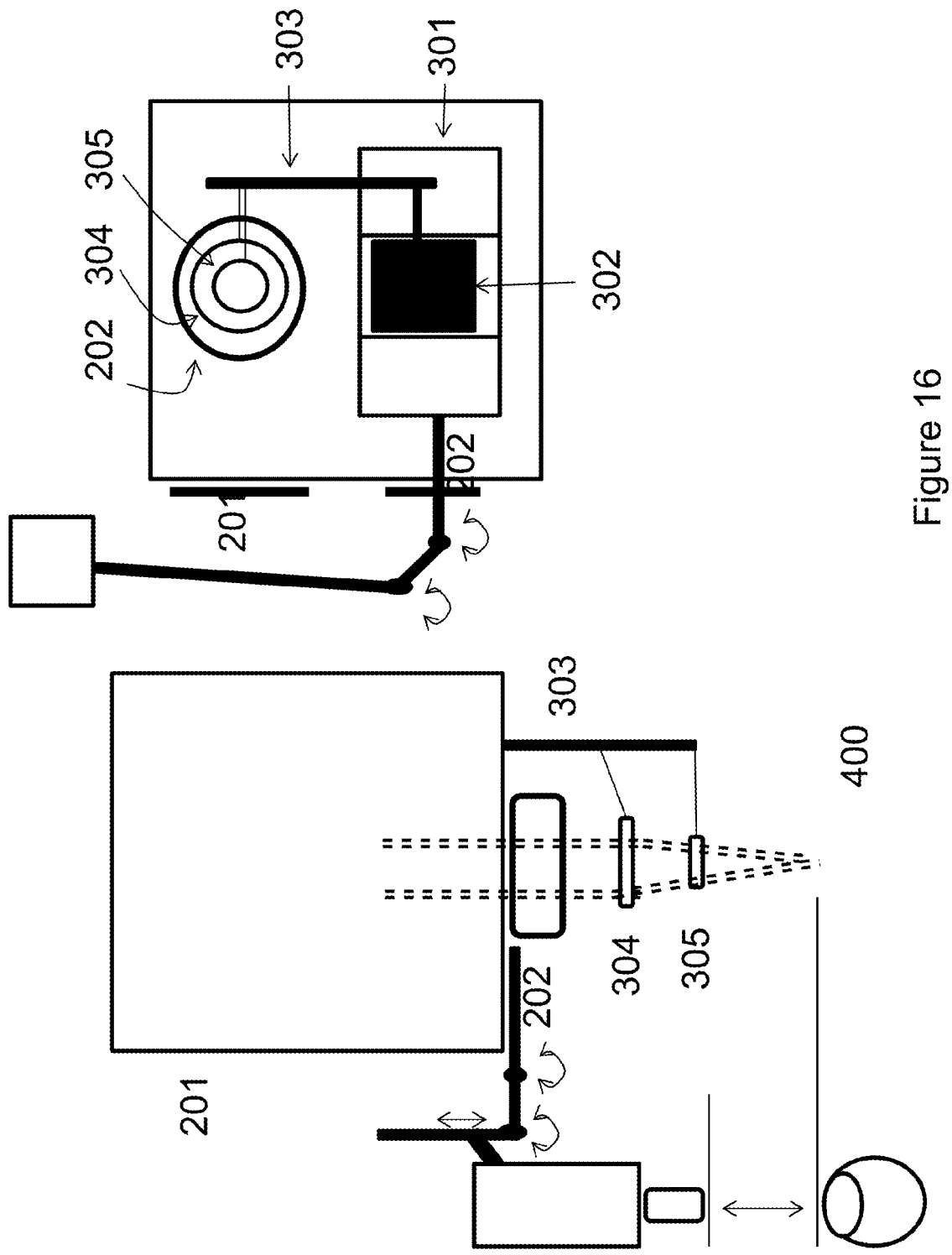
FIG. 16 is a block diagram illustrating a position of an imaging head with respect to the body of the microscope in accordance with some embodiments of the present inventive concept.

Referring now to FIG. 16, a diagram illustrating a position of an imaging head with respect to the body of the microscope will be discussed. As illustrated in FIG. 16, in these embodiments, the OCT imaging path is not coaxial with the microscope head in conjunction with the rotation. Furthermore, lift capabilities of the accessory frame may be used to align the OCT imaging path to the subject.

Accessory frames in accordance with some embodiments may be mountable such that rotation is to the left or the right of a surgeon and may rotate approximately 180 degrees on a half plane perpendicular to the optical axis to the left or the right of the surgeon.

Furthermore, when not in use, the mounted head may be rotated approximately 180 degrees away from the surgeon, and approximately ninety degrees away from any observer stationed along the corresponding half plane. However, when in use the distance from the microscope optical axis and the independent imaging head optical axis may be determined by a user thereof.

The accessory frame 190 may have a height that can be adjusted to position a distal surface of an imaging head objective lens equal to or above a distal surface of the microscope objective lens. The height may also be adjusted to position the distal surface of the imaging head objective lens at an appropriate working distance with respect to the patient eye for proper imaging. As used herein, "an appropriate working distance" refers to the distance from the distal most surface of the OCT imaging head including lens to the proximal most surface of the subject, with the intent of providing adequate visualization of the subject and, when necessary, adequate physical access to the subject.

In some embodiments, the height adjustment may be used to set the working distance to from about 5.0 mm to about 100 mm.

Some embodiments of the accessory frame 190 may be constructed of at least some sterilized or sterilizable materials suitable for use within the surgical sterile field. Furthermore, in some embodiments at least some autoclavable or disposable materials suitable for use within the surgical sterile field may be used.

Figure 8:
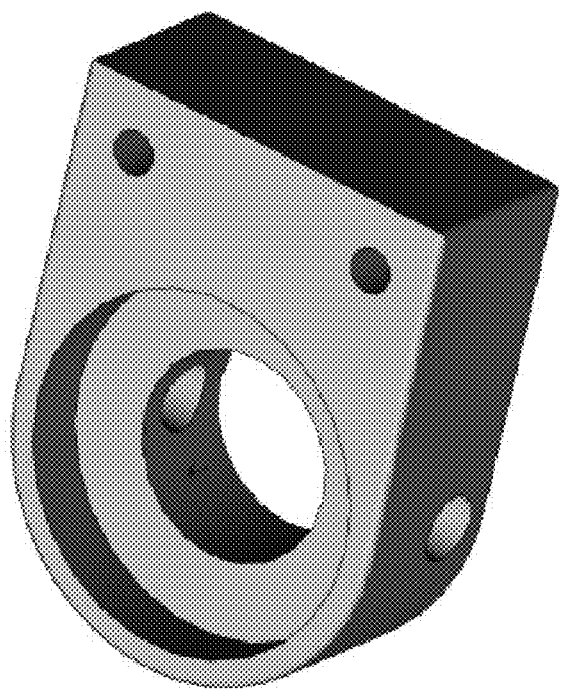
FIGS. 8 and 9 are diagrams illustrating upper and lower portions of a debris trap of the accessory frame in accordance with some embodiments of the present invention.
Figure 9:
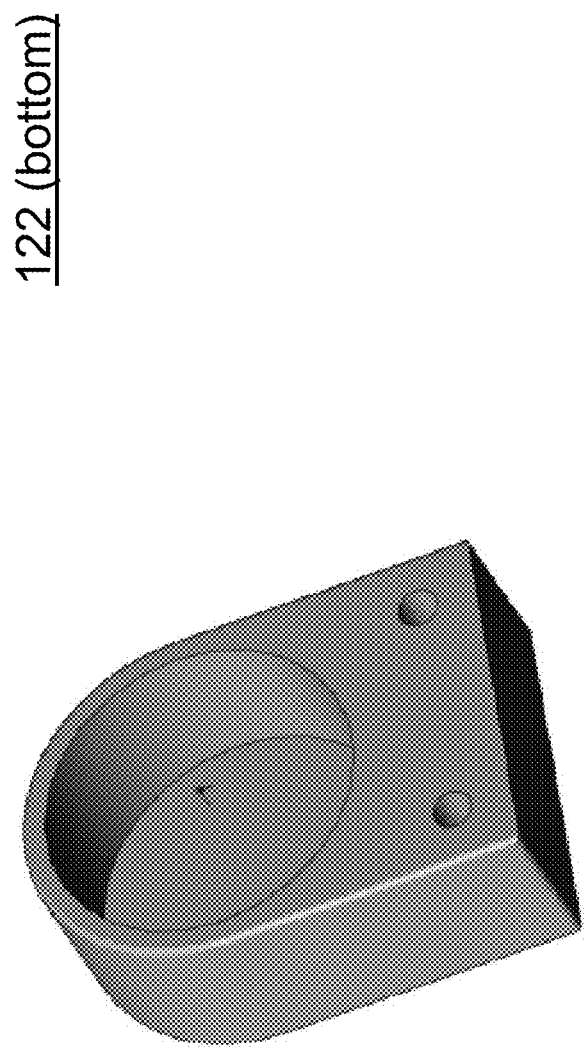

As illustrated in FIG. 1 and further discussed with respect to FIGS. 8 and 9, the accessory frame may include debris traps to catch any materials that may abrade from the structure during motion, rotations, lifts, and the like, while within a sterile field.

Some embodiments of the present inventive concept are configured to be maneuverable with or without the intermediate field lens in place, without requiring any interaction with the intermediate field lens.

The accessory frame 190 may have one or more points of rapid connect/disconnect to allow simple, and in some embodiments, single-handed removal of either the entire frame or the mounted imaging head, without requiring any interaction with or disruption of the intermediate field lens assembly.

As further illustrated in FIG. 1, the accessory frame includes a ballast 180 to balance the weight of the frame plus the imaging head. The ballast 180 may be applied to the half-plane opposite of the mounting of the frame and imaging head. The ballast may be weighted such that the torque applied by the frame and imaging head is offset by the ballast.

Figure 5:
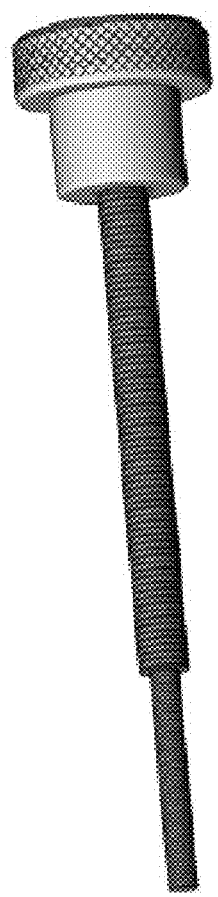
FIG. 5 is a diagram illustrating an anchor pin of an intermediate field lens assembly in accordance with some embodiments of the present inventive concept.
Figure 6:
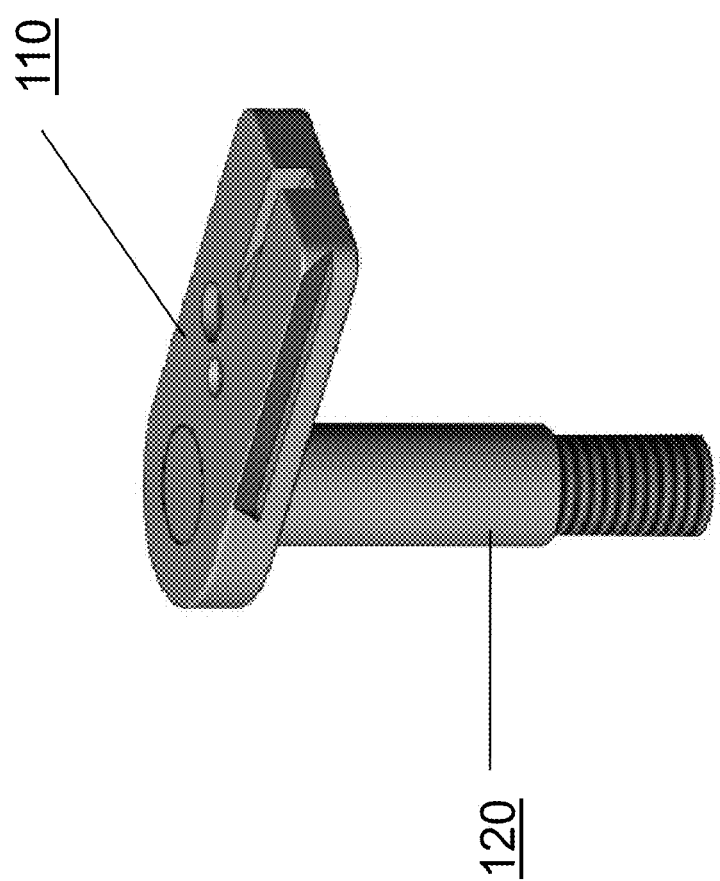
FIG. 6 is a diagram illustrating an accessory frame quick connect plate and first rotation axle of the accessory frame in accordance with some embodiments of the present invention.

Referring now to FIG. 5, a diagram illustrating an anchor pin 102 of an intermediate field lens assembly in accordance with some embodiments of the present inventive concept will be discussed. As illustrated in FIG. 1, the anchor pin 102 (accessory frame quick connect lock) connects the mounting plate 100 to the accessory frame quick connect plate 110, which is illustrated in FIG. 6. As illustrated in FIG. 6, the accessory frame quick connect plate 110 is connected to the first rotation axle 120. The anchor pin 102, and all such like devices that are part of the frame system, may be mechanically captive, such that the pin can release the connection to the frame without coming free of the mounting plate.

Figure 7:
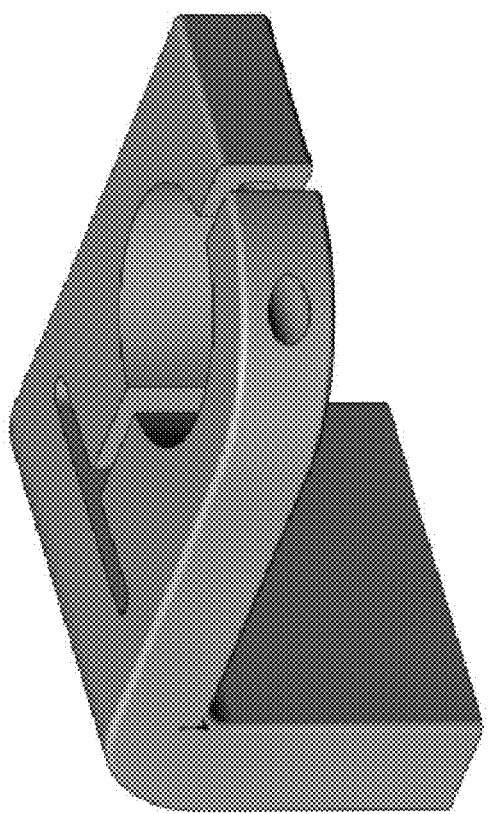
FIG. 7 is a diagram illustrating an instrument carriage of the accessory frame in accordance with some embodiments of the present invention.

FIG. 7 is a diagram illustrating an instrument carriage 140 of the accessory frame in accordance with some embodiments of the present invention. As illustrated in FIG. 1, the second rotations axle 130 extends through the instrument carriage 140, the elevation wheel 132 (illustrated in FIG. 12), and the instrument carriage quick connect mount 150 to the rotation axle bridge 170.

FIGS. 8 and 9 are diagrams illustrating upper and lower portions of a debris trap of the accessory frame in accordance with some embodiments of the present invention. As illustrated in FIG. 1, the upper and lower portions of the debris trap 122 are separated by the rotation axle bridge 170 and the first rotation axle 120 extends through the upper and lower portions of the debris trap 122.

Figure 10:
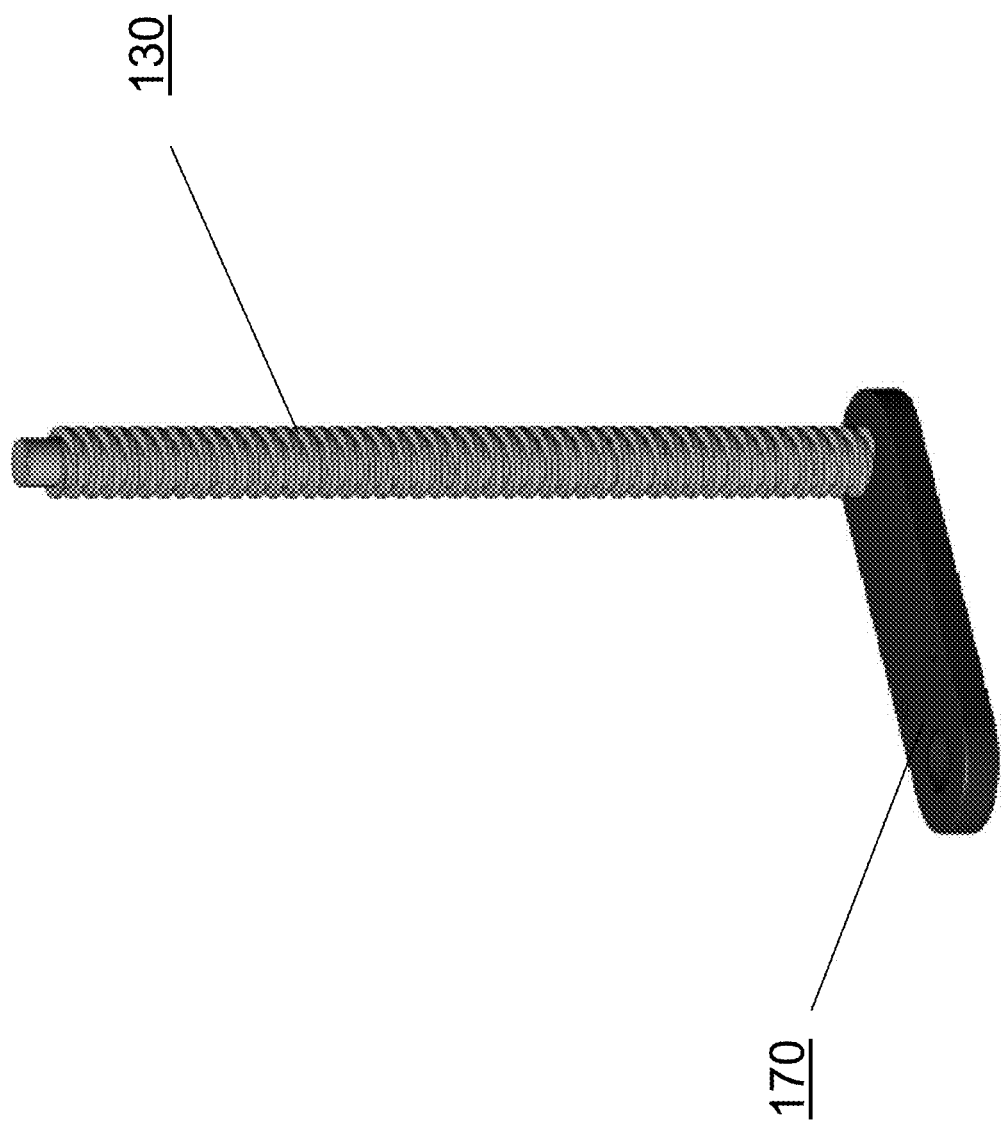
FIG. 10 is a diagram illustrating a second rotation axle and a rotation axle bridge of the accessory frame in accordance with some embodiments of the present invention.

FIG. 10 is a diagram illustrating the second rotation axle 13—and the rotation axle bridge 170 of the accessory frame in accordance with some embodiments of the present invention.

Figure 11:
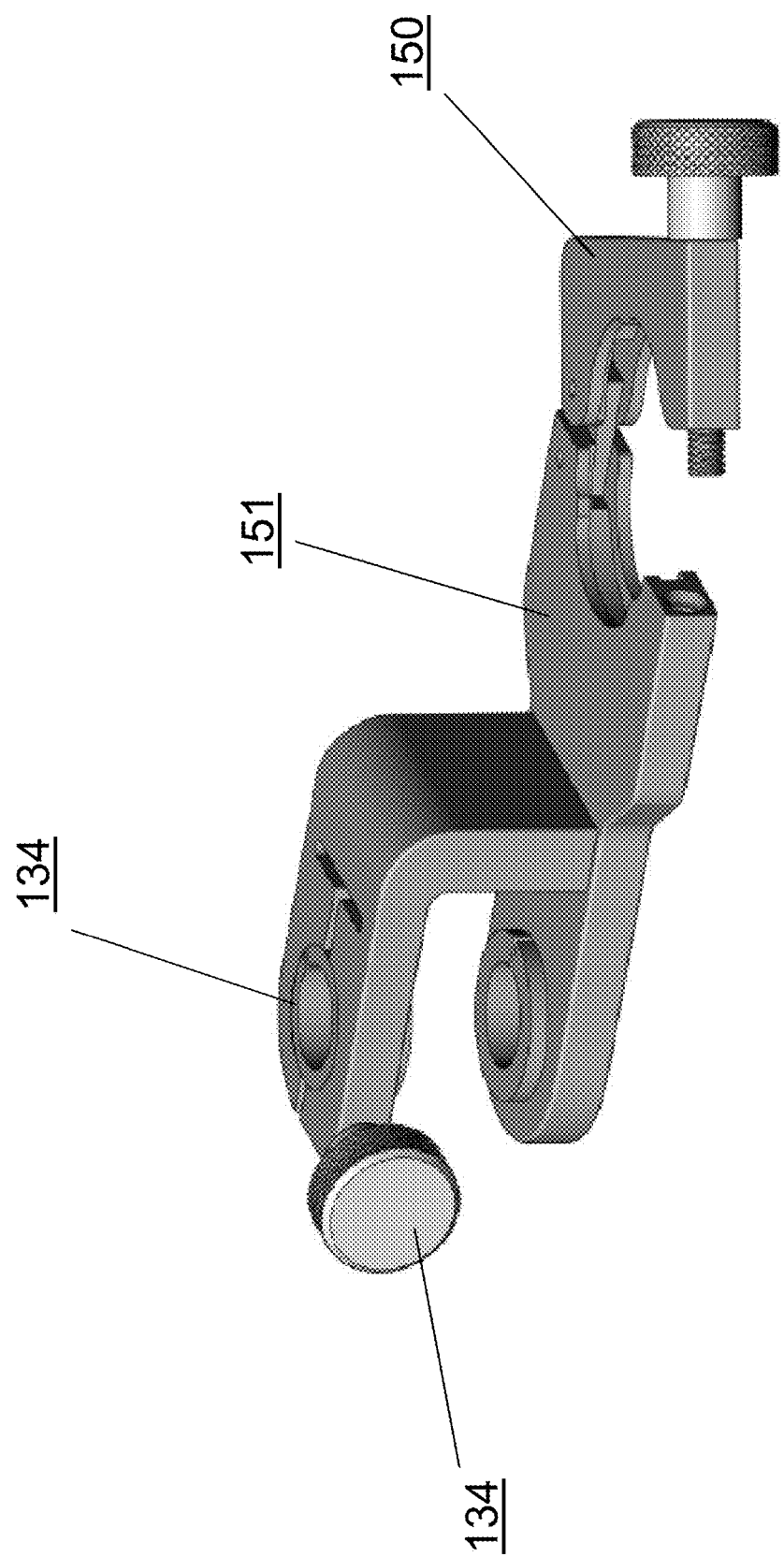
FIG. 11 is a diagram illustrating an instrument carriage quick connect instrument mount of the accessory frame in accordance with some embodiments of the present invention.
Figure 12:
FIG. 12 is a diagram illustrating an elevation wheel of the accessory frame in accordance with some embodiments of the present invention.

FIG. 11 is a diagram illustrating an instrument carriage quick connect instrument mount 150 of the accessory frame in accordance with some embodiments of the present invention. As illustrated in FIG. 11, the instrument carriage quick connect instrument mount 150 has first 150 and second 151 portions. These portions 150, 151 are connected to the instrument carriage 140 and the second rotation lock 134.

Figure 13:
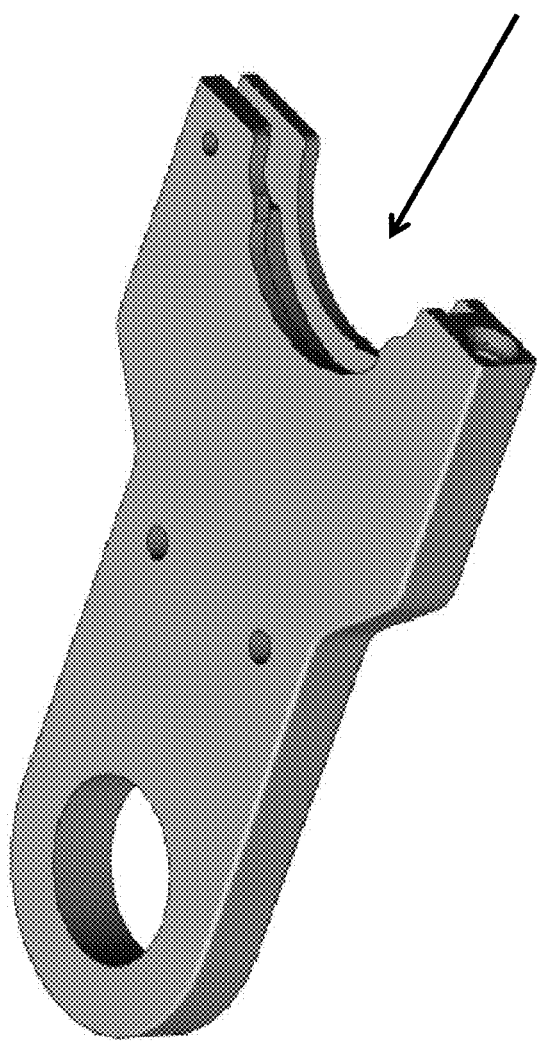
FIGS. 13 and 14 are diagrams illustrating portions of the instrument carriage quick connect instrument mount in accordance with some embodiments of the present invention.
Figure 14:
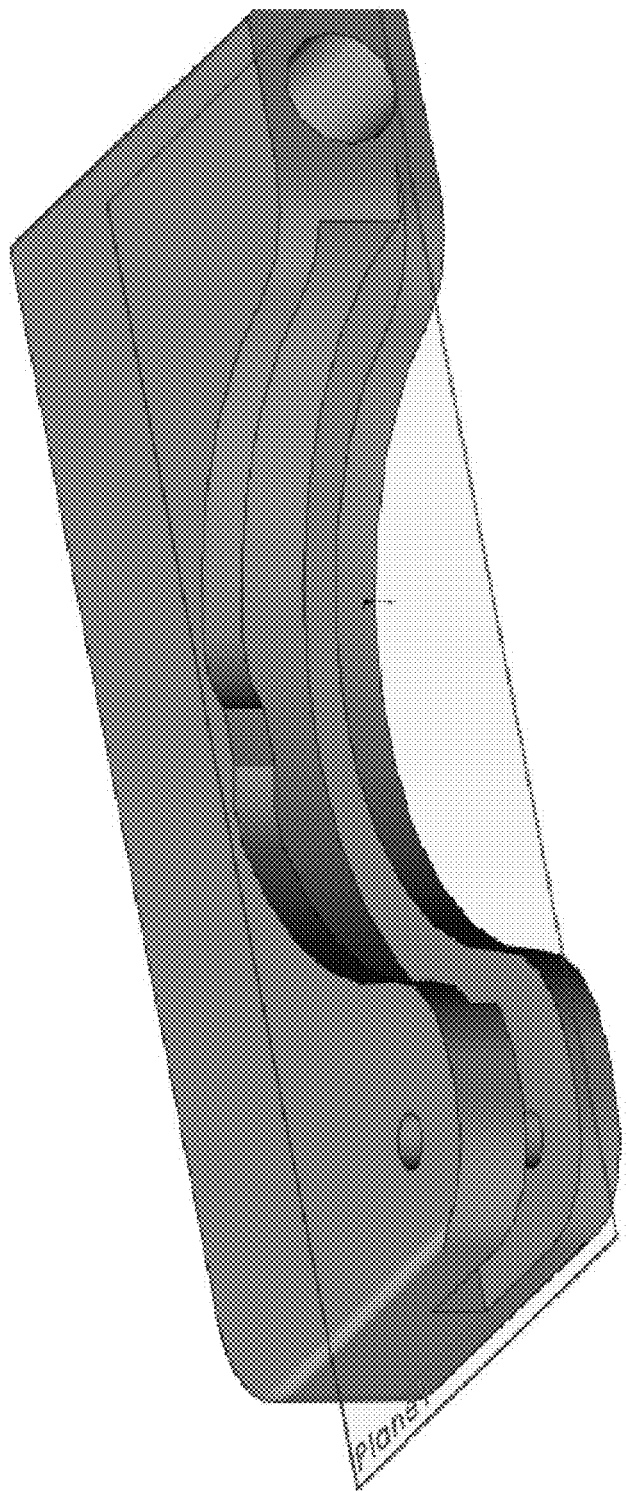

FIGS. 13 and 14 are diagrams illustrating portions of the instrument carriage quick connect instrument mount 150 in accordance with some embodiments of the present invention. In particular, FIG. 13 illustrates the second portion 151 of the instrument mount and FIG. 14 illustrates a front view of the attachment port thereof.

Figure 17:
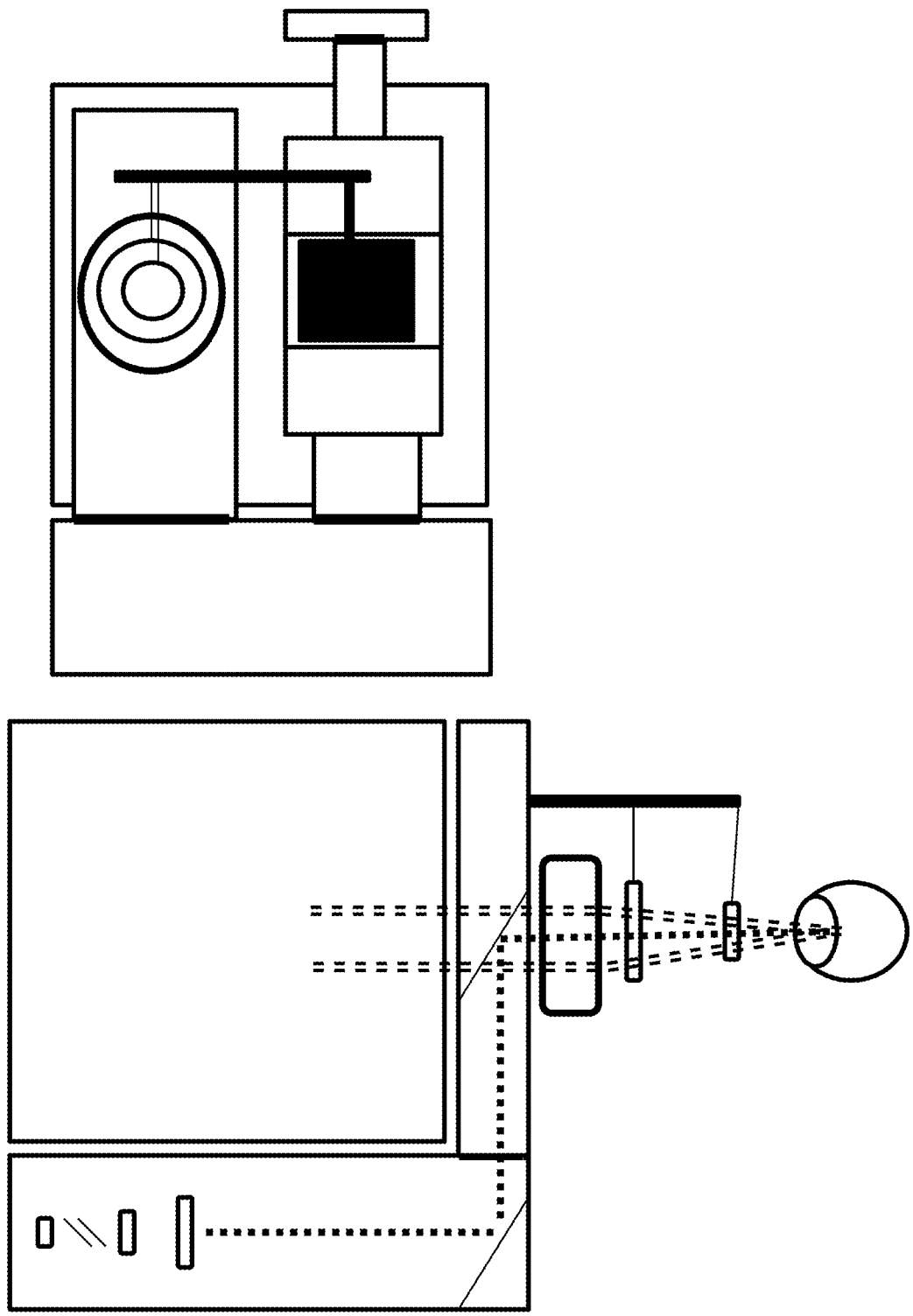
FIG. 17 is a diagram illustrating accessory frames in accordance with some embodiments of the present inventive concept.

Referring now to FIG. 17, a block diagram illustrating frame construction in accordance with some embodiments will be discussed. The frame construction illustrated therein incorporates the OCT imaging head in such a way as to interject the scanning OCT into the path of the surgical microscope, such that the OCT signal shares the surgical microscope objective 202, and the OCT signal and the surgical imaging field are substantially coaxial. In these embodiments, the OCT imaging head is connected to the mounting carriage similarly to the manner in which the accessory frame would be connected to the mounting carriage. The microscope objective is removed from the body of the microscope and attached to the underbody of the OCT imaging head.

In the drawings and specification, there have been disclosed exemplary embodiments of the invention. However, many variations and modifications can be made to these embodiments without substantially departing from the principles of the present invention. Accordingly, although specific terms are used, they are used in a generic and descriptive sense only and not for purposes of limitation, the scope of the invention being defined by the following claims.

That which is claimed is:

1. An accessory frame for selectively coupling components to an optical microscope for imaging of a subject, the optical microscope having a body including an undercarriage, the accessory frame comprising:
   a mounting plate that attaches to the undercarriage of the microscope, the mounting plate comprising:
   a first attachment port and a second attachment port,
   wherein the first attachment port is configured to couple a first optical assembly in an optical path of the microscope between an objective lens of the microscope and the subject; and
   wherein the second attachment port is configured to couple a second optical assembly to the microscope body with at least a portion of the optical path of the second optical assembly being outside of the optical path of the microscope.

2. The accessory frame of claim 1, wherein the second optical assembly comprises an imaging head of an optical coherence tomography imaging system.

3. The accessory frame of claim 1, wherein the first optical assembly comprises a reducing lens and an objective lens positioned along the optical path between the objective lens of the microscope and the subject.

4. The accessory frame of claim 1, wherein the second attachment port of the mounting plate is positioned at a substantially right angle to the first attachment port.

5. The accessory frame of claim 1, wherein the optical microscope is a surgical microscope.

* * * * *